United States Patent [19]

Dusza et al.

[11] 4,374,988

[45] Feb. 22, 1983

[54] 4-HETEROARYLIMIDAZO-[1,5-A]PYRIMIDINES

[75] Inventors: John P. Dusza; Jay D. Albright, both of Nanuet, N.Y.

[73] Assignee: American Cyanamid Company, Stamford, Conn.

[21] Appl. No.: 318,611

[22] Filed: Nov. 5, 1981

[51] Int. Cl.³ .................. C07D 521/00; A61K 31/505
[52] U.S. Cl. .................................. 544/281; 424/251; 542/421; 546/278; 548/336
[58] Field of Search ......................................... 544/281

[56] References Cited

U.S. PATENT DOCUMENTS 3,105,834 10/1963 Wei ..................................... 544/281
4,153,695 5/1979 Turner ................................ 544/281
4,178,449 12/1979 Dusza et al. ....................... 544/281
4,236,005 11/1980 Dusza et al. ....................... 544/281

OTHER PUBLICATIONS

Novinson, et al., "Journal of Heterocyclic Chemistry," vol. 11, No. 6, 1974, pp. 873-878.

Primary Examiner—Donald G. Daus
Assistant Examiner—James H. Turnipseed

Attorney, Agent, or Firm—Mary-Ellen M. Timbers; Edward A. Conroy, Jr.

[57] ABSTRACT

Novel pyrimidine compounds are disclosed of the class represented by the formula:

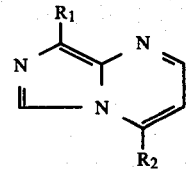

wherein $R_1$ is selected from the class consisting essentially of hydrogen, chloro, bromo, cyano (—CN), carbamoyl (—CO—NH$_2$), carboxyl (—COOH), and lower alkoxycarbonyl (—CO—O—R$_3$, where R$_3$ is a lower alkyl radical having 1-4 carbon atoms), and wherein $R_2$ is a monovalent radical selected from the class consisting essentially of furyl, thienyl, 3-pyridyl and 3-pyridyl-N-oxide, either of said pyridyl radicals optionally being substituted with an alkyl radical having from 1 to 4 carbon atoms. Processes of preparing such compounds are disclosed.

The novel compounds are useful as anxiolytic agents in ameliorating anxiety in a mammal.

16 Claims, No Drawings

4-HETEROARYLIMIDAZO-[1,5-A]PYRIMIDINES

FIELD OF THE INVENTION

This invention relates to novel organic compounds named imidazo-[1,5-a]pyrimidines, to their therapeutic use as anxiolytic agents, and to processes for the synthesis of such compounds.

Prior Art

The applicants are not aware of any prior art patents or publications which, in their respective judgment, should be deemed to anticipate the compounds or processes described and claimed herein. By way of background, U.S. Pat. No. 4,236,005 is cited.

BRIEF SUMMARY OF THE INVENTION

The pyrimidines compounds of this invention include those of the class represented by formula (11):

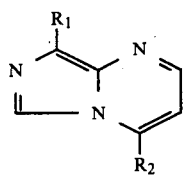

wherein $R_1$ is selected from the class consisting essentially of hydrogen, chloro, bromo, cyano (—CN), carbamoyl (—CO—NH$_2$), carboxyl (—COOH), and lower alkoxycarbonyl (—CO—O—$R_3$, where $R_3$ is a lower alkyl radical having 1-4 carbon atoms), and wherein $R_2$ is a monovalent radical selected from the class consisting essentially of furyl, thienyl, 3-pyridyl and 3-pyridyl-N-oxide, either of said pyridyl radicals optionally being substituted with an alkyl radical having from 1 to 4 carbon atoms.

The structures of the monovalent 3-pyridyl and 3-pyridyl-N-oxide moieties are depicted as:

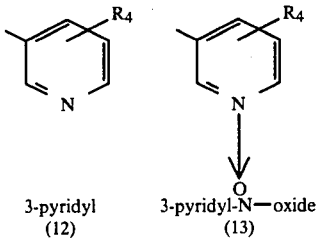

3-pyridyl (12)     3-pyridyl-N—oxide (13)

wherein $R_4$ is selected from the class consisting essentially of hydrogen and lower alkyl having from 1 to 4 carbon atoms.

As is later referred to herein, $R_5$ is defined as selected from the class consisting essentially of cyano, carbamoyl, carboxyl, and the above-defined lower alkoxycarbonyl, and as such in a sub-set of $R_1$. $R_6$ is defined as being selected from the class consisting of hydrogen, chloro, bromo, cyano, carbamoyl and lower alkoxycarbonyl, and as such in a second sub-set of $R_1$.

The various subscripts and symbols for chemical moieties, once defined herein, continue to have the same definition.

The novel compounds invention are crystalline materials having characteristic melting points and absorption spectra, and typically vary from colorless to yellow. They are appreciably soluble in many organic solvents, such as lower alkanols, chloroform, tetrahydrofuran, N,N-dimethylformamide and the like, but are generally relatively insoluble in water.

The invention also comprises processes of preparing compounds within the scope of formula 11, wherein $R_1$ is cyano, by a reaction of a 5[[2-($R_2$)vinyl]-amino]-4-imidazole-3-carboxamide (formula 17A on Flowchart I) with a dehydration and ring closure reagent. Reagents having such capabilities are known in the art and include phosphorus oxychloride (a preferred reagent), phosphorus trichloride, phosphorus pentachloride, a phosphoric anhydride, such as $P_2O_5$ or polyphosphoric acid, boran trifluoride, aluminum trichloride and lower alkyl (or substituted alkyl) anhydrides, such as acetic anhydride or trifluoroacetic anhydride.

The 5[[2-($R_2$)vinyl]-amino]-4-imidazole-3-carboxamide (formula 17A) may be made by reacting a 3-di(-lower alkyl)amino-1-($R_2$)-2-propen-1-one (having formula 15, depicted on Flowchart I) and a 4-amino-5-imidazole-3-carboxamide (formula 16A). As referred to herein, compounds of formula 16 refer to the free base or an acid salt thereof.

The invention also comprises processes of preparing compounds within the scope of formula 11, wherein $R_1$ is limited to $R_5$, by reacting at an elevated temperature a 3-di(lower alkyl)-amino-1-($R_2$)-2-propen-1-one (formula 15) and a 3-($R_5$)-4-amino-imidazole with a lower alkanoic acid, such as acetic acid, propanoic acid or butanoic acid.

The novel compounds are useful as anxiolytic agents in a process of ameliorating anxiety in a mammal, which process comprises administering to a mammal a therapeutically effective amount of a compound represented by formula 18, or a mixture of such compounds.

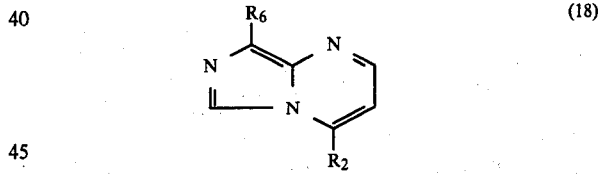

The compound 4-(3-pyridyl)imidazo[1,5-a]pyrimidine-8-carbonitrile (i.e., a compound of formula 18 wherein $R_6$ is cyano and $R_2$ is 3-pyridyl) is preferred for such a process.

In the following description, compounds of formulas 11, 16 and 17 having specific $R_1$ substituents are referred to by a suffix letter following their compound formula number, as follows:

| $R_1$ | Suffix Letters For Compounds Of Formulas 11, 16 and 17 |
|---|---|
| carbamoyl | A |
| cyano | B |
| carboxyl | C |
| H | D |
| chloro or bromo | E |
| lower alkoxy carbonyl | F |
| $R_5$ | G |

DETAILED DESCRIPTION

The novel compounds may be prepared by a plurality of processes, the first of which is explained in conjunction with Flowchart I.

about 16 hours, to produce a 3-di(lower alkyl)-amino-1-$R_2$-2-propen-1-one of formula 15.

The compound of formula 15 is then reacted, in Step 1-2, with a 4-amino-5-imidazole-3-carboxamide of formula 16A in an inert solvent to produce a 5-[[2-$R_2$)vinyl]amino]-4-imidazole-3-carboxamide of formula 17A. The reaction is conducted at an elevated temperature, such as on a steam bath, for one to several hours. The carboxamide of formula 16A may be in the form of the free base but is preferably in the form of the hydrochloride salt as shown on Flowchart I.

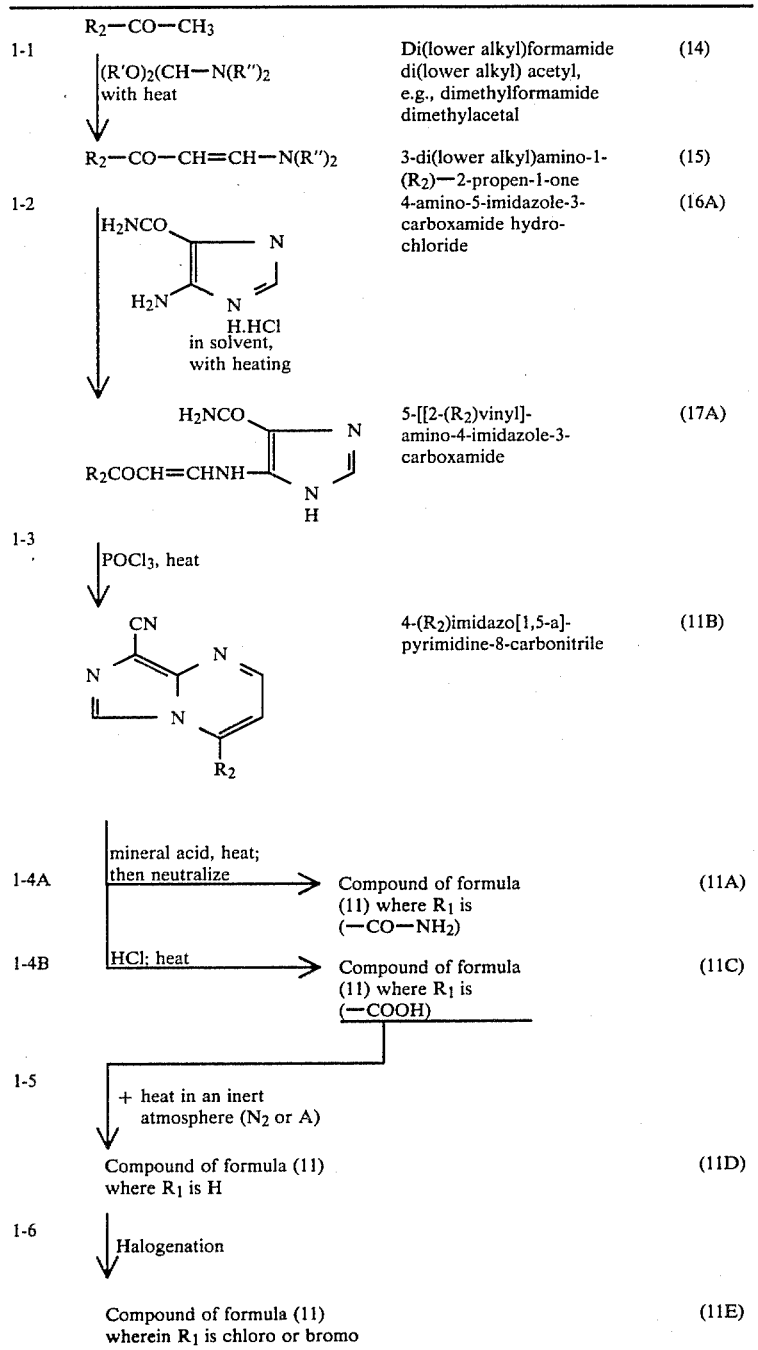

In accordance with the process scheme depicted in Flowchart I, the novel imidazo[1,5-a]pyrimidines can be prepared by reacting (in Step 1—1) an heteroaryl acetyl compound with a di(lower alkyl) formamide di(lower alkyl) acetal of formula 14, e.g., dimethylformamide dimethylacetal, at an elevated temperature in the range of about 50° C. to about 150° C. for about 4 to The phrase "inert solvent" as employed herein includes, illustratively, dioxane, dichloromethane, $C_6$–$C_9$ aromatics and tetrahydrofuran, and others which will be readily understood by persons skilled in pharmaceutical chemistry.

The carboxamide of formula 17A is reacted, in Step 1-3, with a Lewis acid at an elevated temperature to produce the corresponding 4-$R_2$-imidazo[1,5-a]pyrimidine-8-carbonitrile of formula 11B. The Lewis acid is preferably $POCl_3$ but may alternatively be selected from the class consisting essentially also of phosphorus trichloride, phosphorus pentachloride, a phosphoric anhydride, such as $P_2O_5$ or a polyphosphoric acid, boron trifluoride, aluminum trichloride and lower alkyl (or substituted alkyl) anhydrides, such as acetic anhydride or trifluoroacetic anhydride. The reaction is conducted for several hours at an elevated temperature, for example, at reflux conditions. Any remaining volatile matter is removed under vacuum, and then ice and an inert solvent such as dichloromethane is added to the remaining reaction mixture. The organic layer is washed with aqueous sodium hydroxide, then dried over a desiccant, such as anhydrous sodium sulfate, and n-hexane is added to precipitate the product.

The carbonitrile of formula 11B can be converted, in Step 1-4A, to the corresponding 8-carboxamide compound of formula 11A by reaction with a strong mineral acid, such as sulfuric acid, and any excess acid neutralized.

Alternatively, the 8-carbonitrile of formula 11B can be converted, in Step 1-4B, to an 8-carboxylic acid of formula 11C by reaction with a mineral acid at an elevated temperature, optionally in the presence of an alkali metal salt of a lower alkanoic acid, e.g., sodium acetate.

If desired, the 8-carboxylic acid of formula 11C may be decarboxylated, in Step 1-5, by heating at an elevated temperature in the range of about 150°–350° C. under an inert atmosphere, such as nitrogen or argon, until the evolution of carbon dioxide is no longer observed. The reaction mixture is cooled, dissolved in an inert solvent, and dried. The mixture is heated to reflux and the product 4-($R_2$)imidazo[1,5-a]pyrimidine (formula 11D) crystallized by the gradual addition of a lower alkane, such as n-hexane.

The decarboxylated pyrimidine of formula 11D can optionally be halogenated, in Step 1-6, by reaction with an N-chloro- or N-bromo-cycloimide, such as N-bromosuccinimide or N-chlorobenzotriazole, to produce an 8-chloro- or 8-bromopyrimidine compound of formula 11E. The reaction is advantageously conducted at an elevated temperature in an inert solvent. After the reaction, the mixture is added to cold (about 0° C.) concentrated aqueous sodium hydroxide; the organic layer is then dried, then refluxed, and the product precipitated by the gradual addition of a lower alkane.

Alternatively, the compounds of formula 11G, wherein $R_1$ is replaced by $R_5$, may be prepared by reacting a 3-di-(lower alkyl)amino-1-$R_2$-2-propen-1-one of formula 15 with a 3-$R_5$-4-amino-5-imidazole of formula 16G and a lower alkanoic acid at an elevated temperature to obtain a 4-$R_2$-imidazo-[1,5-a]-pyrimidine-8-$R_5$ of formula 11G. The reaction is conducted at an elevated temperature in the range of about 50° C. to about 150° C., advantageously in the range of about 100°–125° C., for a period of time ranging from a few hours to one day, with the time required being inversely related to the temperature employed. If it is desired to make the 8-carboxamide product (where $R_5$ is carbamoyl), the reaction is advantageously conducted in the presence of sodium acetate. Where $R_5$ is cyano or a lower alkoxycarbonyl, and the desired product is the pyrimidine-8-carbonitrile of formula 11B, or the 8-lower alkyl ester of formula 11F, respectively, the reaction is advantageously conducted in an inert solvent such as dichloromethane.

The novel compounds of this invention possess central nervous system activity at non-toxic doses and as such are useful as anxiolytic agents. They produce certain responses in standard tests with laboratory animals which are understood to correlate well with relief of anxiety in man.

The anti-anxiety properties of the novel compounds of the invention have been established in a test which indicates anxiolytic activity by the measure of protection from convulsions resulting from the administration of pentylenetetrazole (sold as METROZOL, Reg. T.M.). Single or graded dosage levels of the test compounds were administered orally or intraperitoneally (in a 2% starch vehicle, containing 5% v/v polyethylene glycol and one to two drops of polysorbate 80) to groups of at least 4 rats. Thirty or 60 minutes after administration, the rats were treated intravenously with pentylenetetrazole at a dosage of 23 mg/kg. of body weight. This dose is estimated to cause clonic seizures in 99% of unprotected rats. A test compound is considered active if it protects 50% or more of the rats from clonic seizures. It has been reported (R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pages 237–288 (1971)) that there is a high degree of correlation between antagonism of pentylenetetrazole seizures in rats and anti-anxiety effects in higher mammals. A representative compound of the present invention, 4-(3-pyridyl)-imidazo[1,5-a]-pyrimidine-8-carbonitrile, has been shown to possess anxiolytic activity when tested as described above.

Another test which has been employed to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, Vol. 21, pages 1–7 (1971). A conflict situation is induced in rats by a modification of this method. The test is referred to herein as the "thirsty rat conflict" test.

Groups of 8 naive, Wistar strain rats, weighing 200-240 g. each, were deprived of water for 48 hours. The test compounds were administered in single or graded, oral or intraperitoneal doses, suspended in distilled water and one drop of polysorbate 80. The control animals received the vehicle alone. After 30 or 60 minutes, each rat was placed in an individual clear plexiglass chamber. Tap water was available ad libitum from a nipple located in a black plexiglass box adjacent to the main chamber. A circuit carrying a 0.7 milliampere AC shocking current was established between the stainless steel grid floor of the chamber and the nipple. After 20 licks of non-shocked drinking, a fixed ratio of a 2-second "shock-on" and 19 licks "shock-off" cycle began and continued for a total of 3 minutes. The number of shocks taken by each rat during a 3-minute interval was recorded and compared to a control group. The test compounds are considered active if the number of shocks received by the test group is significantly higher than the control group by the Mann-Whitney U test. 4-(3-Pyridyl)imidazo[1,5-a]pyrimidine-8-carbonitrile has been shown to possess anxiolytic activity when tested as described above.

Another test utilized for the determination of anxiolytic activity is the measurement of the ability of test compound to inhibit the binding of tritiated benzodiazepines to brain-specific receptors of mammals. A modification of the method described by R. F. Squires, et al., Nature, Vol. 266, No. 21, page 732 (1977) and H. Mohler, et al., Science, Vol. 198, page 849 (1977) was employed.

Male albino rats (Wistar strain, weighing 150–200 g. each) were obtained from Royalhart Farms. $^3$H-methyl-flunitrazepam (84.3 Ci/mmol) was obtained from New England Nuclear. The test compounds were solubilized in dimethylformamide.

Whole cortex of rats was homogenized gently in 10 volumes of ice-cold 0.32 M. sucrose, centrifuged twice at 1000 g. for 10 minutes and then recentrifuged at 30,000 g. for 20 minutes to produce a crude $P_2$-synaptosomal fraction. The $P_2$-fraction was resuspended in 10 volumes of 10 mM Tris.HCl (pH 7.5) and frozen ($-20°$ C.) until time of use. Frozen $P_2$-fractions were thawed and resuspended in eighty time the original homogenizing volume at time of assay.

The binding assay consisted of 300 $\mu$l. of the $P_2$-fraction suspension (0.1–0.3 mg. protein), 100 $\mu$l. of test drug and 100 $\mu$l. of $^3$H-flunitrazepam (1.0 mM., final concentration) which was added to 1.5 ml. of 50 mM Tris.HCl (pH 7.5). Non-specific binding controls and total binding controls received 100 $\mu$l. of clonazepam (1 $\mu$M. final concentration) and 100 $\mu$l. of buffer, respectively, in place of the test compound. Incubation for 30 minutes proceeded in ice (0° C.) and was terminated by filtration, under vacuum, through Whatman GF/C glass fiber filters. The filters were washed twice with 5 ml. of ice-cold 50 mM Tris.HCl (pH 7.5) and placed in scintillation vials. Ten ml. of Beckman Ready-Solve HP was added and the radioactivity determined in a Beckman Scintillation Counter.

Compounds which exhibit the ability to inhibit $^3$H-benzodiazepine binding by 20% at (1 $\mu$M. concentration) are considered to be active. Inhibition of binding is calculated by the difference between specific binding with no drug and specific binding in the presence of test compound, divided by the specific binding with no drug, X 100.

The novel compounds of the present invention have been found to be highly useful for meliorating anxiety in mammals when administered in amounts ranging from about 0.1 mg. to about 35.0 mg./kg. of body weight per day. A preferred dosage regimen for optimum results would be from about 0.5 mg. to about 5.0 mg./kg. of body weight per day. Such dosage units are employed that a total of from about 35 mg. to about 1.0 g. of active compound for a subject of about 70 kg. of body weight are administered in a 24-hour period. This dosage regimen may be titrated to provide the optimum therapeutic response. For example, several divided doses may be administered daily or the dose may be proportionally reduced as indicated by the exigencies of the therapeutic situation. The compounds of this invention are preferably administered orally but may be administered in any convenient manner, such as by intravenous, intramuscular, or subcutaneous means.

Compositions according to the present invention having the desired clarity, stability and adaptability for parenteral use are obtained by dissolving from 0.01% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above-described vehicles may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, parenteral solutions may also contain various preservatives which may be employed to prevent bacterial and fungal contamination. The preservatives which may be used for such purposes are, for example, myristyl-gamma-picolinium chloride, benzalkonium chloride, phenethyl alcohol, p-chlorophenyl-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain: a binder, such as gum tragacanth, acacia, corn starch or gelatin; excipients such as dicalcium phosphate; a disintegrating agent, such as corn starch, potato starch, alginic acid and the like; a lubricant such as magnesium stearate; and a sweetening agent, such as sucrose, lactose or saccharin may be added or a flavoring agent such as peppermint, oil of wintergreen, or cherry flavoring. When the dosage unit form is a capsule, it may contain, in addition to the foregoing materials, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl- and propyl-parabens as preservatives, a dye, and flavoring such as cherry or orange flavor. Of course, any material used in preparing any dosage unit form should be pharmaceutically pure and substantially nontoxic in the amounts employed.

The invention will be described in greater detail in conjunction with the following illustrative specific examples.

EXAMPLE 1

4-(2-Thienyl)imidazo[1,5-a]pyrimidine-8-carbonitrile

Part A

A mixture of 10.0 g. of 2-acetylthiophene and 15.0 g. of N, N-dimethylformamide dimethylacetal was heated at reflux under anhydrous conditions for 16 hours. The solvent was removed in vacuo. Upon the addition of n-hexane, a crystalline product was obtained. The product was recrystallized from dichloromethane-hexane to produce 9.15 g. of 3-dimethylamino-1-(2-thienyl)-2-propen-1-one, m.p. 114°–115° C.

Part B

A mixture of 9.06 g. of the propen-1-one compound, as prepared above, in 50 ml. of p-dioxane was added to a solution of 8.14 g. of 4-amino-5-imidazolecarboxamide hydrochloride in 50 ml. of water. This mixture was heated on a steam bath for 2 hours, water was added to achieve turbidity, and upon cooling a precipitate was separated and collected by filtration to produce 4.80 g. of 5-[[2-(2-thenoyl)vinyl]amino]-4-imidazolecarboxamide as a yellow solid, m.p. 145°–150° C.

Part C

Four grams of the imidazolecarboxamide, as prepared above, was heated at reflux with 40 ml. of phosphorus oxychloride for 6 hours. The volatiles were removed from the reaction mixture in vacuo and ice was added to the residue, followed by dichloromethane. The organic layer was washed with 1 N sodium hydroxide and dried over anhydrous sodium sulfate. n-Hexane was added to separate the product, which was collected by filtration to produce 0.97 g. of 4-(2-thienyl)imidazo[1,5-a]pyrimidine-8-carbonitrile as yellow needles, m.p. 257°–259° C.; UV$\lambda_{max}^{0.1\ N\ HCl}$228($\epsilon$, 26,700), 264($\epsilon$, 7,240), 307($\epsilon$, 7,690), 376($\epsilon$, 8,150); IR(KBr), 222(CN), 1613, 1541, 1517 cm$^{-1}$; PMR (d$_6$-DMSO), $\delta$ 3.23(s), 7.32(m), 8.08(m), 8.62(m), 8.84(s).

When evaluated in the thirsty rat conflict test, this compound was active when administered intraperitoneally at a dosage of 25 mg,/kg. It produced 39% inhibition when evaluated for ability to inhibit $^3$H-benzodiazepine by the procedure described above. When administered intraperitoneally at a dosage of 50 mg./kg. for resistance to convulsions induced by pentylenetetrazole, the compound was considered to be inactive.

Part D

Alternatively, a solution of 1.08 of 5-aminoimidazole-4-carbonitrile (prepared as described in Japanese patent 6910 (1967); Chemical Abstracts, 68, 68995n (1968)) and 1.81 g. of 3-dimethylamino-1-(2-thienyl)-2-propen-1-one in 25 ml. of glacial acetic acid can be refluxed for 6 hours. The solvent can be removed at reduced pressure and the residue recrystallized from dichloromethane-hexane, as described in Part C above, to give the same product as described in Part C.

EXAMPLE 2

4-(3-Thienyl)imidazo[1,5-a]pyrimidine-8-carbonitrile

When 3-acetylthiophene was substituted for 2-acetylthiophene in Part A of Example 1, 3-dimethylamino-1-(3-thienyl)-2-propen-1one, m.p. 89°–90° C., was obtained as the product.

Reaction of 5.44 g. of the above product with 4.86 g. of 4-amino-5-imidazolecarboxamide hydrochloride as in Part B of Example 1, gave 5.60 g. of 5-[[2-(3-thenoyl)-vinyl]amino]-4-imidazolecarboxamide as a yellow solid, m.p. 135°–137° C.

Cyclization and amide dehydration of 4.0 g. of the preceding compound with 50 ml. of phosphorus oxychloride in the manner described in Part C of Example 1 yielded 4-(3-thienyl)imidazo[1,5-a]pyrimidine-8-carbonitrile as short yellow needles, m.p. 297°–299° C.; UV$\lambda_{max}^{0.1\ N\ HCl}$ 225($\epsilon$, 29,420), 288($\epsilon$, 9,690), 365($\epsilon$, 9,240), IR(KBr), 2291(CN), 1613, 1550, 1520 cm$^{-1}$; PMR (d$_6$-DMSO), $\delta$ 3.24(d), 7.76(m), 7.86(m), 8.52(m), 8.66(d), 8.72(s).

This compound produced 20% inhibition when evaluated for ability to inhibit $^3$H-benzodiazepine.

EXAMPLE 3

4-(2-Furyl)imidazo[1,5-a]pyrimidine-8-carbonitrile

As in Example 1, Part A, when 5.0 g. of 2-acetylfuran is reacted with 10 ml. of N,N-dimethylformamide dimethylacetal, 3-dimethylamino-1-(2-furyl)-2-propen-1-one can be produced as tan crystals, m.p. 84°–86° C.

By reacting 0.01 mol of the above product with 0.01 mol of 4-amino-5-imidazolecarboxamide hydrochloride in dioxane-water as described in Part B of Example 1, 5-[[2-(2-furoyl)vinyl]amino]-4-imidazolecarboxamide can be prepared as a high melting yellow solid.

Cyclization and amide dehydration of 0.01 mol of the preceding compound with 10 ml. of phosphorus oxychloride under the conditions described in Part C of Example 1 can provide 4-(2-furyl)imidazo[1,5-a]pyrimidine-8-carbonitrile as a high melting solid.

EXAMPLE 4

4-(3-Furyl)imidazo[1,5-a]pyrimidine-8-carbonitrile

As in Example 1, Part A, 0.01 mol of 3-acetylfuran can be reacted with 0.02 mol of N,N-dimethylformamide dimethylacetal to produce 3-dimethylamino-1-(3-furyl)-2-propen-1-one.

The above solid can be reacted with an equal molar amount of 4-amino-5-imidazolecarboxamide hydrochloride as described in Part B of Example 1 to produce 5-[[2-(3-furoyl)vinyl]amino]-4-imidazolecarboxamide as a red-orange solid.

Cyclization and dehydration of 0.01 mol of the preceding compound with phosphorus oxychloride as described in Part C of Example 1, can produce 4-(3-furyl)imidazo[1,5-a]pyrimidine-8-carbonitrile as a high melting yellow solid.

EXAMPLE 5

4-(3-Pyridyl)imidazo[1,5-a]pyrimidine-8-carbonitrile

In accordance with Example 1, Part A, 0.1 mole of 3-acetylpyridine was reacted under reflux with a slight excess of N,N-dimethylformamide dimethylacetal; 3- dimethylamino-1-(3-pyridyl)-2-propen-1-one was isolated as a solid, m.p. 66°–67° C.

Reaction of 0.01 mol of the preceding compound with 0.01 mol of 4-amino-5-imidazolecarboxamide hydrochloride in p-dioxane-water under the conditions described in Part B of Example 1 gave 5-[[(3-pyridyl)-vinyl]amino]-4-imidazolecarboxamide, which was collected by filtration.

When 5.0 g. of the above compound was refluxed with 50 ml. of phosphorus oxychloride in the manner outlined in Part C of Example 1, 4-(3-pyridyl)imidazo[1,5-a]pyrimidine-8-carbonitrile was obtained as yellow needles, m.p. 258°–260° C.; UV $\lambda_{max}^{0.1\ N\ HCl}$ 216($\epsilon$, 28,090), 225($\epsilon$, 5,950), 336($\epsilon$, 2,340); IR(KBr) 2234(CN), 1625, 1587, 1531 cm$^{-1}$.

When evaluated in the thirsty rat conflict test, this compound was found to be active when administered orally at a dosage of 25 mg./kg. It produced 19% inhibition when evaluated for ability to inhibit $^3$H-benzodiazepine. It was effective for resistance to convulsions induced by pentylenetetrazole, requiring a dosage of 6.8 mg./kg. to be effective in 50% of the rats when administered orally (i.e., an ED$_{50}$ of 6.8 mg./kg.

EXAMPLE 6

4-(2-Thienyl)imidazo[1,5-a]pyrimidine-8-carboxamide

A mixture of 0.01 mol of 3-dimethylamino-1-(2-thienyl)-2-propen-1-one (prepared as described in Example 1, Part A), 0.01 mol of 4amino-5-imidazolecarboxamide hydrochloride and 0.01 mol of anhydrous sodium acetate in 25 ml. of glacial acetic acid can be refluxed for 16 hours. The reaction mixture can be cooled and the crystalline precipitate collected by filtration and washed with water to produce 4-(2-thienyl)imidazo[1,5-a]pyrimidine-8-carboxamide.

EXAMPLE 7

4-(3-Thienyl)imidazo[1,5-a]pyrimidine-8-carboxamide

3-Dimethylamino-1-(3-thienyl)-2-propen-1-one (prepared as described in Example 2) can be substituted for 3-dimethylamino-1-(2-thienyl)-2-propen-1-one in the procedure of Example 6, to produce 4-(3-thienyl)imidazo[1,5-a]pyrimidine-8-carboxamide.

EXAMPLE 8

4-(2-Furyl)imidazo[1,5-a]pyrimidine-8-carboxamide

3-Dimethylamino-1-(2-furyl)-2-propen-1-one (prepared as described in Example 3) can be substituted for 3-dimethylamino-1-(2-thienyl)-2-propen-1-one in the procedure of Example 6, to produce 4-(2-furyl)imidazo[1,5-a]pyrimidine-8-carboxamide.

EXAMPLE 9

4-(3-Furyl)imidazo[1,5-a]pyrimidine-8-carboxamide

3-Dimethylamino-1-(3-furyl)-2-propen-1-one (prepared as described in Example 4) can be substituted for 3-dimethylamino-1-(2-thienyl)-2-propen-1-one (prepared as described in Example 4) in the procedure of Example 6, to produce 4-(3-furyl)imidazo[1,5-a]pyrimidine-8-carboxamide.

EXAMPLE 10

4-(3-Pyridyl)imidazo[1,5-a]pyrimidine-8-carboxamide

3-Dimethylamino-1-(3-pyridyl)-2-propen-1-one (prepared as described in Example 5) can be substituted for 3-dimethylamino-1-(2-thienyl)-2-propen-1-one in the procedure of Example 6, to produce 4-(3-pyridyl)imidazo[1,5-a]pyrimidine-8-carboxamide.

EXAMPLE 11

Ethyl 4-(2-thienyl)imidazo[1,5-a]pyrimidine-8-carboxylate

A mixture of 1.55 g. (0.01 mols) of ethyl 4-amino-5-imidazolecarboxylate and 1.81 g. (0.01 mols) of 3-dimethylamino-1-(2-thienyl)-2-propen-1-one (prepared as described in Example 1, Part A) in 25 ml. of glacial acetic acid can be refluxed for 16 hours, then cooled and evaporated to dryness in vacuo. The residue can be dissolved in dichloromethane and passed through a short column of hydrous magnesium silicate. The effluent can be refluxed on a steam bath with a slow constant addition of n-hexane. At the first appearance of crystallization, heating should be curtailed and the solution allowed to cool. The precipitated material can be collected by filtration to produce ethyl 4-(2-thienyl)imidazo[1,5-a]pyrimidine-8carboxylate.

EXAMPLE 12

Ethyl 4-(3-thienyl)imidazo[1,5-a]pyrimidine-8-carboxylate

3-Dimethylamino-1-(3-thienyl)-2-propen-1-one (prepared as described in Example 2) can be substituted for 3-dimethylamino-1-(2-thienyl)-2-propen-1-one in the procedure of Example 11, to produce ethyl 4-(3-thienyl)imidazo[1,5-a]pyrimidine-8-carboxylate.

EXAMPLE 13

Ethyl 4-(2-furyl)imidazo[1,5-a]pyrimidine-8-carboxylate

By substituting 3-diethylamino-1-(2-furyl)-2-propen-1-one (prepared as described in Example 3) for 3-dimethylamino-1-(2-thienyl)-2-propen-1-one in the procedure of Example 11, one can produce ethyl 4-(2-furyl)imidazo[1,5-a]pyrimidine-8-carboxylate.

EXAMPLE 14

Ethyl 4-(3-furyl)imidazo[1,5-a]pyrimidine-8-carboxylate

3-Dimethylamino-1-(3-furyl)-2-propen-1-one (prepared as described in Example 4) can be substituted for 3-dimethylamino-1-(2-thienyl)-2-propen-1-one in the procedure of Example 11, to produce ethyl 4-(3-furyl)imidazo[1,5-a]pyrimidine-8-carboxylate.

EXAMPLE 15

Ethyl 4-(3-pyridyl)imidazo[1,5-a]pyrimidine-8-carboxylate

When 3-dimethylamino-1-(3-pyridyl)-2-propen-1-one (prepared as described in Example 5) was substituted for 3-dimethylamino-1-(2-thienyl)-2-propen-1-one in the procedure of Example 11, ethyl 4-(3-pyridyl)imidazo[1,5-a]pyrimidine-8-carboxylate was obtained as colorless crystals, mp. 184°–186° C.; UV $\lambda_{max}^{0.1\ N\ HCl}$ 223($\epsilon$, 20,390), 280($\epsilon$, 8,590), 358($\epsilon$, 3,960); IR(KBr) 1700(C=O) cm$^{-1}$; PMR (CDCl$_3$), $\delta$ 1.48($\epsilon$, C$\underline{H}_3$CH$_2$O), 4.58(q, CH$_3$C$\underline{H}_2$O), 6.86(d), 7.32(s), 7.66(m), 8.07(m), 8.16(s), 8.66(s), 9.0(m).

This compound produced a 49% inhibition when evaluated for ability to inhibit the effect of $^3$H-benzodiazepine. The compound was considered to be inactive in the thirsty rat conflict procedure when administered orally at a dosage of 25 mg./kg.

EXAMPLE 16

4-(2-Thienyl)imidazo[1,5-a]pyrimidine-8-carboxylic acid

A mixture of 0.01 mol of 4-(2-thienyl)imidazo[1,5-a]pyrimidine-8-carbonitrile (Example 1), 15 ml. of glacial acetic acid and 15 ml. of concentrated hydrochloric acid can be refluxed for 16 hours. The reaction mixture can be cooled and evaporated to dryness in vacuo, water added, and the precipitated solid recovered by filtration to produce 4-(2-thienyl)imidazo[1,5-a]pyrimidine-8-carboxylic acid.

EXAMPLE 17

4-(3-Thienyl)imidazo[1,5-a]pyrimidine-8-carboxylic acid 4-(3-Thienyl)imidazo[1,5-a]pyrimidine-8-carbonitrile (prepared as described in Example 2) can be substituted for 4-(2-thienyl)imidazo[1,5-a]pyrimidine-8-carbonitrile in the procedure of Example 16, to produce (4-(3-thienyl)imidazo[1,5-a]pyrimidine-8-carboxylic acid.

EXAMPLE 18

4-(2-Furyl)imidazo[1,5-a]pyrimidine-8-carboxylic acid 4-(2-Furyl)imidazo[1,5-a]pyrimidine-8-carbonitrile (prepared as described in Example 3) can be subsstituted for 4-(2-thienyl)imidazo[1,5-a]pyrimidine-8-carbonitrile in the procedure of Example 16, to produce 4-(2-furyl)imidazo[1,5-]-pyrimidine-8-carboxylic acid.

EXAMPLE 19

4-(3-Furyl)imidazo[1,5-a]pyrimidine-8-carboxylic acid

4(3-Furyl)imidazo[1,5-a]pyrimidine8-carbonitrile (prepared as described in Example 4) can be substituted for 4-(2-thienyl)imidazo[1,5-]pyrimidine-8-carbonitrile in the procedure of Example 16, to produce 4-(3-furyl)imidazo[1,5-a]pyrimidine-8-carboxylic acid.

EXAMPLE 20

4-(3-Pyridyl)imidazo[1,5-a]pyrimidine-8-carboxylic acid 4-(3-Pyridyl)imidazo[1,5-a]pyrimidine-8-carbonitrile (prepared as described in Example 5) can be substituted for 4-(2-thienyl)imidazo[1,5-a]pyrimidine-8-carbonitrile in the procedure of Example 16, to produce 4-(3-pyridyl)imidazo[1,5-a]pyrimidine-8-carboxylic acid.

EXAMPLE 21

4-(2-Thienyl)imidazo[1,5-]pyrimidine

A 5.0 g. sample of 4-(2-thienyl)imidazo[1,5-a]-pyrimidine-8-carboxylic acid (prepared as described in Example 16) can be placed in a reaction flask. The flask can be evacuated, and charged with argon or nitrogen, placed in an oil bath and heated at 180°–250° C. for as long as the evolution of carbon dioxide can be observed. The flask can then be cooled and the residue can be dissolved in dichloromethane. The resulting solution can be passed through a short column of hydrous magnesium silicate. The effluent can be heated to reflux with the gradual addition of n-hexane until crystallization can be observed. The mixture can then be cooled and the precipitate collected by filtration to produce 4-(2-thienyl)imidazo[1,5-]pyrimidine.

EXAMPLE 22

4-(3-Thienyl)imidazo[1,5-a]pyrimidine 4-(3-Thienyl)imidazo[1,5-]pyrimidine-8-carboxylic acid (prepared as described in Example 17) can be substituted for 4-(2-thienyl)imidazo[1,5-a]pyrimidine-8-carboxylic acid in the procedure of Example 21, to produce 4-(3-thienyl)imidazo[1,5-]pyrimidine.

EXAMPLE 23

4-(2-Furyl)imidazo[1,5-a]pyrimidine 4-(2-Furyl)imidazo[1,5-a]pyrimidine-8-carboxylic acid (prepared as described in Example 18) can be substituted for 4-(2-thienyl)imidiazo[1,5-a]pyrimidine-8-carboxylic acid in the procedure of Example 21, to produce 4-(2-furyl)imidazo[1,5-a]pyrimidine.

EXAMPLE 24

4-(3-Pyridyl)imidazo[1,5-a]pyrimidine 4-(3-Pyridyl)imidazo[1,5-a]pyrimidine-8-carboxylic acid (prepared as described in Example 20) can be substituted for 4-(2-thienyl)imidazo[1,5-a]pyrimidine-8-carboxylic acid in the procedure of Example 21, to produce 4-(3-pyridyl)imidazo-[1,5-a]pyrimidine.

EXAMPLE 25

8-Chloro-4-(3-pyridyl)imidazo[1,5-a]pyrimidine

A mixture of 0.01 mol of 4-(3-pyridyl)imidazo[1,5-a]pyrimidine (prepared as described in Example 24) and N-chlorosuccinimide (0.013 mol) in 50 ml. of dichloromethane can be refluxed on a steam bath for 3 hours. The reaction mixture can be poured into 100 ml. of ice cold 2.5 N sodium hydroxide solution, the organic layer separated, and dried over anhydrous sodium·sulfate, and then passed through a short column of hydrous magnesium silicate. The effluent can be refluxed on a steam bath with the gradual addition of n-hexane until crystallization occurs. The mixture can be cooled and the desired product collected by filtration to produce 8-chloro-4-(3-pyridyl)imidazo[1,5-a]pyrimidine.

EXAMPLE 26

8-Bromo-4-(3-pyridyl)imidazo[1,5-a]pyrimidine

N-bromosuccinimide can be substituted for N-chlorosuccinimide in the procedure of Example 25, to produce 8-bromo-4-(3-pyridyl)imidazo[1,5-a]pyrimidine.

Having thus described the invention, what is claimed is:

1. Compounds having the formula wherein $R_1$ is selected from the class consisting essentially of hydrogen, chloro, bromo, cyano (—CN), carbamoyl (—CO—NH$_2$), carboxyl (—COOH), and lower alkoxycarbonyl (—CO—O—R$_3$, where R$_3$ is a lower alkyl radical having 1–4 carbon atoms), and wherein $R_2$ is a monovalent radical selected from the class consisting essentially of furyl, thienyl, 3-pyridyl and 3-pyridyl- N-oxide, either of said pyridyl radicals optionally being substituted with an alkyl radical having from 1 to 4 carbon atoms.

2. Compounds of claim 1 wherein $R_2$ is furyl or thienyl.

3. Compounds of claim 1 wherein $R_1$ is selected from the class consisting essentially of cyano, chloro or bromo, and $R_2$ is furyl or thienyl.

4. Compounds of claim 2 wherein $R_1$ is lower alkoxycarbonyl having from 2 to 4 carbon atoms.

5. Compounds of claim 1 wherein $R_1$ is carbamoyl.

6. The compound of claim 1 wherein $R_1$ is cyano and $R_2$ is 2-thienyl.

7. The compound of claim 1 wherein $R_1$ is cyano and $R_2$ is 3-thienyl.

8. The compound of claim 1 wherein $R_1$ is carbamoyl and $R_2$ is thienyl.

9. The compound of claim 1 wherein $R_1$ is chloro and $R_2$ is thienyl.

10. Compounds of claim 1 wherein $R_2$ is 3-pyridyl.

11. Compounds of claim 10 wherein $R_2$ is 3-pyridyl substituted with lower alkyl.

12. Compounds of claim 1 wherein $R_2$ is 3-pyridyl and $R_1$ is selected from the class consisting essentially of cyano, chloro and bromo.

13. Compounds of claim 1 wherein $R_2$ is 3-pyridyl and $R_1$ is lower alkoxycarbonyl having 2 to 4 carbon atoms.

14. The compound of claim 1 wherein $R_2$ is 3-pyridyl and $R_1$ is cyano.

15. The compound of claim 1 wherein $R_2$ is 3-pyridyl and $R_1$ is carbamoyl.

16. The compound of claim 1 wherein $R_2$ is 3-pyridyl and $R_1$ is carboxyl.

* * * * *